United States Patent
Morrow et al.

(10) Patent No.: US 6,754,592 B2
(45) Date of Patent: Jun. 22, 2004

(54) INDIRECT MEASUREMENT OF NITROGEN IN A MULTI-COMPONENT NATURAL GAS BY HEATING THE GAS

(75) Inventors: Thomas B. Morrow, San Antonio, TX (US); Kendricks A. Behring, II, Torrance, CA (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 10/460,579

(22) Filed: Jun. 12, 2003

(65) Prior Publication Data

US 2004/0019436 A1 Jan. 29, 2004

Related U.S. Application Data

(63) Continuation-in-part of application No. 09/550,431, filed on Apr. 17, 2000, now Pat. No. 6,604,051.

(51) Int. Cl.[7] .............................................. G01N 31/00
(52) U.S. Cl. .............................. 702/27; 702/23; 702/24
(58) Field of Search ............................ 702/22, 23, 24, 702/25–27, 137, 138, 150, 156, 98–99; 73/24.01, 24.05, 24.06, 54.02, 54.24, 61.45, 61.47

(56) References Cited

U.S. PATENT DOCUMENTS

| | | | |
|---|---|---|---|
| 4,489,592 A | 12/1984 | Pacanowski et al. | 73/30 |
| 4,596,133 A | 6/1986 | Smalling et al. | 73/24 |
| 5,285,675 A | 2/1994 | Colgate et al. | 73/23.2 |
| 5,311,447 A | 5/1994 | Bonne | 364/609 |
| 5,486,107 A | 1/1996 | Bonne | 431/12 |
| 5,537,854 A | 7/1996 | Phillips et al. | 73/24.01 |
| 5,932,793 A | 8/1999 | Dayton et al. | 73/24.05 |
| 6,047,589 A | 4/2000 | Hammond et al. | 73/24.01 |
| 6,065,328 A | 5/2000 | Dayton et al. | 73/25.01 |
| 6,076,392 A * | 6/2000 | Drzewiecki | 73/23.2 |
| 6,209,387 B1 | 4/2001 | Savidge | 73/24.05 |
| 6,286,360 B1 | 9/2001 | Drzewiecki | 73/24.01 |

FOREIGN PATENT DOCUMENTS

| | | | | |
|---|---|---|---|---|
| DE | 198 23 193 A1 | 11/1999 | | G01N/9/00 |
| EP | 1 063 525 A2 | 7/1999 | | G01N/33/22 |
| EP | 0 939 317 A2 | 9/1999 | | G01N/33/22 |
| EP | 0 959 354 A2 | 11/1999 | | G01N/33/22 |
| WO | WO 93/08457 | 4/1993 | | G01N/9/00 |
| WO | WO 99/10740 | 3/1999 | | G01N/33/22 |

OTHER PUBLICATIONS

U.S. Pending Continuation–in–Part patent application Ser. No. 10/401,206 entitled "Indirect Measurement of Nitrogen in a Multi–Component Gas by Measuring the Speed of Sound at Two States of the Gas", filed by Thomas B. Morrow et al., filed Mar. 27, 2003.

U.S. Pending Continuation–in–Part patent application Ser. No. 10/237,492 entitled "A System and Method to Determine Thermophysical Properties of a Multi–Component Gas at Arbitrary Temperature and Pressure", filed by Thomas B. Morrow et al., filed Sep. 9, 2002.

Wild, K.R., "Controlling Processes that are Sensitive to Natural Gas Quality", presented at the 21st World Gas Conference, Nice France, Jun. 6–9, 2000.

PCT/US01/12217 Search Report, Mailed Nov. 13, 2001.

PCT/US01/12217 International Preliminary Examination Report, Jul. 8, 2002.

* cited by examiner

Primary Examiner—Bryan Bui
(74) Attorney, Agent, or Firm—Baker Botts L.L.P.

(57) ABSTRACT

Methods of indirectly measuring the nitrogen concentration in a natural gas by heating the gas. In two embodiments, the heating energy is correlated to the speed of sound in the gas, the diluent concentrations in the gas, and constant values, resulting in a model equation. Regression analysis is used to calculate the constant values, which can then be substituted into the model equation. If the diluent concentrations other than nitrogen (typically carbon dioxide) are known, the model equation can be solved for the nitrogen concentration.

9 Claims, 3 Drawing Sheets

| GAS MIXTURE CHARACTERISTIC | RANGE OF GAS MIXTURE CHARACTERISTIC |
|---|---|
| MOLECULAR WEIGHT, $M$ [LBM/LB-MOL] | 16.33 - 19.52 |
| IDEAL SPECIFIC GRAVITY, $G_{id}$ [$M$/28.9625] | 0.564 - 0.674 |
| STANDARD VOLUMETRIC HEATING VALUE $H_{v,std}$ [BTU/REAL SCF AT 60°F, 14.73 PSIA] | 987 - 1150 |
| $C_6+$ CONCENTRATION [mol %] | 0.0009 - 0.100 |
| TOTAL DILUENT CONCENTRATION [mol %] | 0.968 - 7.40 |
| METHANE [mol %] | 83.42 - 98.27 |
| ETHANE [mol %] | 0.516 - 9.53 |
| PROPANE [mol %] | 0.161 - 3.57 |
| ISO-BUTANE [mol %] | 0.0355 - 0.647 |
| N-BUTANE [mol %] | 0.0237 - 0.432 |
| ISO-PENTANE [mol %] | 0.0094 - 0.167 |
| N-PENTANE [mol %] | 0.0063 - 0.112 |
| N-HEXANE [mol %] | 0.0003 - 0.0654 |
| N-HEPTANE [mol %] | 0.0000 - 0.0260 |
| N-OCTANE [mol %] | 0.0000 - 0.0235 |
| CARBON DIOXIDE [mol %] | 0.0330 - 6.00 |
| NITROGEN [mol %] | 0.0330 - 6.00 |

INDIRECT MEASUREMENT OF NITROGEN IN A MULTI-COMPONENT NATURAL GAS BY HEATING THE GAS

RELATED APPLICATION

This application is a continuation-in-part from U.S. patent application Ser. No. 09/550,431, filed Apr. 17, 2000 and entitled "System and Method to Determine Thermophysical Properties of a Multi-Component Gas" now U.S. Pat. No. 6,604,051.

GOVERNMENT LICENSE RIGHTS

The U.S. Government has a paid-up license in this invention and the right in certain circumstances to require the patent owner to license others on reasonable terms as provided for by the terms of Contract No. DE-FC21-96MC33033 for the U.S. Department of Energy.

FIELD OF THE INVENTION

This invention relates to the field of measuring constituent components of gas mixtures, and more particularly, to measuring the concentration of nitrogen in a gas mixture.

DESCRIPTION OF THE RELATED ART

U.S. patent application Ser. No. 09/550,431, entitled "System and Method to Determine Thermophysical Properties of a Multi-Component Gas" and U.S. patent application Ser. No. 10/237,492 entitled "A System and Method to Determine Thermophysical Properties of a Multi-Component Gas at Arbitrary Temperature and Pressure" describe systems and methods for measuring heating value and energy flow rates of natural gas. An advantage of these methods is that they do not require a full composition assay. The methods correlate the speed of sound in the gas to the heating value of the gas, which depends on the gas composition, flow temperature, and pressure. The calculations for determining the heating value require known values for the diluent concentrations in the gas, such as carbon dioxide and nitrogen. However, there is no need for other constituent values to be known.

The concentration of nitrogen in a natural gas mixture is difficult to measure directly. Nitrogen has low infrared absorption characteristics, which makes infrared sensing methods difficult. Also, it is chemically inert, which makes electrochemical sensing methods difficult.

Yet, the amount of nitrogen in a gas mixture does affect heating value. Experimentation has indicated that a plus or minus shift of 0.075 mole % in nitrogen concentration will produce a plus or minus shift of 1.0 BTU/SCF in standard volumetric heating value. Thus, to make use of the above-described methods for relating speed of sound and diluent measurements to heating values, some means for measuring nitrogen content is important.

This is but one example of a need for measuring nitrogen content in a natural gas—there may be other applications in which measurement of nitrogen content may be useful. In the absence of satisfactory sensors for direct measurement, indirect measurement methods have been considered.

BRIEF DESCRIPTION OF THE FIGURES

FIG. 1 illustrates the characteristics of an example of a database for correlating molecular weight of natural gas to the speed of sound in the gas.

DETAILED DESCRIPTION OF THE PREFERRED EMBODIMENT

Figure 2:
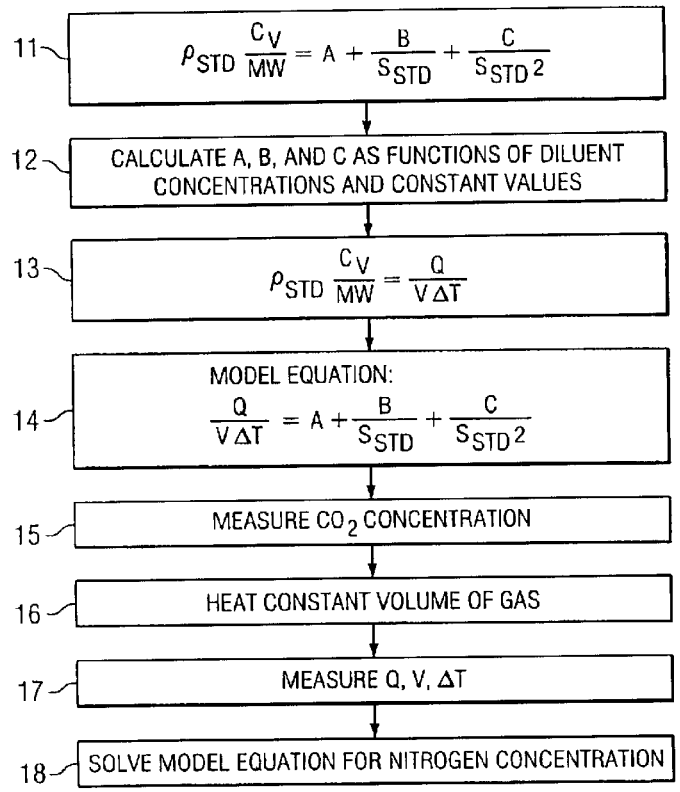
FIG. 2 illustrates a first method of determining the nitrogen concentration in a natural gas.

As stated in the Background, U.S. patent application Ser. No. 09/550,431, entitled "System and Method to Determine Thermophysical Properties of a Multi-Component Gas" and U.S. patent application Ser. No. 10/237,492 entitled "A System and Method to Determine Thermophysical Properties of a Multi-Component Gas at Arbitrary Temperature and Pressure", describe methods for inferentially measuring heating value and energy flow rates of natural gas.

U.S. patent application Ser. No. 09/550,431 further describes methods for inferentially measuring nitrogen. One of the nitrogen measurement methods is further described in U.S. patent application Ser. No. 10/371,419 entitled "Indirect Measurement of Nitrogen in a Multi-Component Natural Gas by Heating the Gas". These patent applications are incorporated by reference herein.

One aspect of the above-described methods is correlation of the speed of sound in the gas to the molecular weight of the gas. The calculations for determining the molecular weight require known values for the diluent concentrations in the gas, such as carbon dioxide and nitrogen, as well as known values for the speed of sound, temperature, and pressure. However, there is no need for other constituent values to be known.

For purposes of this description, the gas mixture is assumed to be a natural gas, whose primary diluent components are carbon dioxide and nitrogen. For natural gases, the method is most accurate when the concentration of other diluent gases is low. The method described herein may be extended to other gases containing nitrogen, if those gases behave similarly to natural gases.

The molecular weight of a natural gas mixture of unknown composition is constant for the specific mixture. However, the molecular weight is quantitatively unknown because the gas constituents are not known.

As explained in U.S. patent application Ser. No. 09/550,431, molecular weight of a mixture plots semi-linear with sound speed, with the scatter in the data (about 1%) being a function of the diluent concentrations. Molecular weight may be represented by the following equation, which relates molecular weight to speed of sound and the diluent gas concentrations:

$$MW = (A + B/S + C/S^2) * (1 + D*X_{CO_2} + E*X_{N_2})$$

where MW is the molecular weight of a gas sample.

The constants A, B, C, D, and E are derived from a database containing reference gas mixtures, whose molecular weights are known. These constants are functions of the gas temperature and pressure, but they are not functions of the gas composition.

FIG. 1 summarizes a database composition range for a set of reference gas compositions. U.S. patent Ser. No. 09/550,431, incorporated by reference above, provides an example of a suitable database, representing 102 unique gas compositions that fall within these ranges. For each reference gas mixture, the speed of sound can be calculated for a matrix of temperature and pressure values. These speed of sound calculations may be performed using commercially available computer software such as SONICWARE, manufactured by Lomic, Inc. By applying statistical methods to the database, values of the constants can be calculated for any given temperature and pressure state.

The database for producing the constant values may also comprise a smaller set of reference gas compositions, selected to be representative of different molecular weights and diluent concentrations. For example, a database of nine reference gas mixtures might comprise three categories of mixtures, one with high molecular weight, one with intermediate molecular weight, and one with low molecular weight. Each category could then comprise three mixtures, such as, one with no diluents, one with nitrogen as the only diluent, and one with carbon dioxide as the only diluent. An example of a suitable diluent concentration for this database would be 2.0 mole % of either nitrogen or carbon dioxide or both. Once a suitable set of reference gases is selected, standard matrix operations for solving algebraic equations can be used to produce values for the constants. For example, the database might comprise nine reference gases, each having a unique value of molecular weight. The sound speeds for each of the nine gases for a range of discrete temperature and pressure values is calculated and stored. As stated above, this calculation can be performed using commercially available software. Then, once the temperature and pressure of the subject natural gas is measured, interpolation can be used to estimate the speed of sound at that state for the reference gases. With nine values of sound speed, nine values of molecular weight, and nine values of CO2 and N2 for the nine reference gases, there is sufficient information to find the values of A, B, C, D and E at that state. As an alternative to storing pre-calculated sound speed values, the sound speeds for the reference gases could be calculated "on the fly" for the measured temperature and pressure, if appropriate programming is incorporated into the run time calculations.

For purposes of this description, standard temperature is 60° F. and standard pressure is 14.73 psia. The variables, $X_{CO2}$, $X_{N2}$, and $S_{std}$ represent the carbon dioxide concentration, nitrogen concentration, and speed of sound at standard temperature and pressure. The speed of sound at standard temperature and pressure is referred to as the "standard sound speed". The values $c_p$ and $c_v$ are molar specific heats (constant volume and constant pressure), measured in units of Btu/lbmole° F. Specific heat, in the context of this description, is evaluated at standard temperature (T) and pressure (P), rather than being a full thermodynamic function of T and P.

Readily-available computer programs may be used to calculate values of $c_p$, $c_v$, and sound speed $S_{std}$, for various natural gas compositions at standard temperature and pressure.

As explained below, the specific heats can be related to properties that are measurable by heating the gas. Then, these properties can be related to speed of sound and diluent concentrations. A first method infers nitrogen concentration by heating the gas at constant volume. A second method infers nitrogen concentration by heating a steady mass flow of the natural gas through a heating tube (constant pressure).

FIG. 2 illustrates a method of indirectly measuring nitrogen concentration in a natural gas by heating a confined sample (constant volume) of the gas. For a known value of $X_{CO2}$, the value of $X_{N2}$ is inferred from the temperature rise and heat energy.

For a gas mixture in a container at standard temperature and pressure, the mass of the gas mixture inside the container is $m=V \rho_{STD}$, where V is the container volume in units of $ft^3$ and $\rho_{STD}$ is the gas mixture density in units of $lbm/ft^3$. The gas is heated using an electrical heater to raise the temperature by an amount $\Delta T$. The amount of electrical energy used to heat the gas can be measured as the product of the voltage across the heater times the current through the heater times the duration of heating in seconds. The gas in the container is heated at constant volume, such that the gas pressure rises slightly as a result of the temperature rise. The gas density within the container does not change because neither the container volume nor the mass of the gas changes. The amount of heat energy, Q, added to the gas in the container (ignoring losses through the cylinder wall) can be calculated as follows:

$$Q=\rho_{STD}*V*(c_v/MW)*\Delta T$$

If Q (the quantity of heat) and $\Delta T$ are measured and V is known, then:

$$(\rho_{STD}*c_v/MW)=Q/(V*\Delta T)$$

Figure 3:
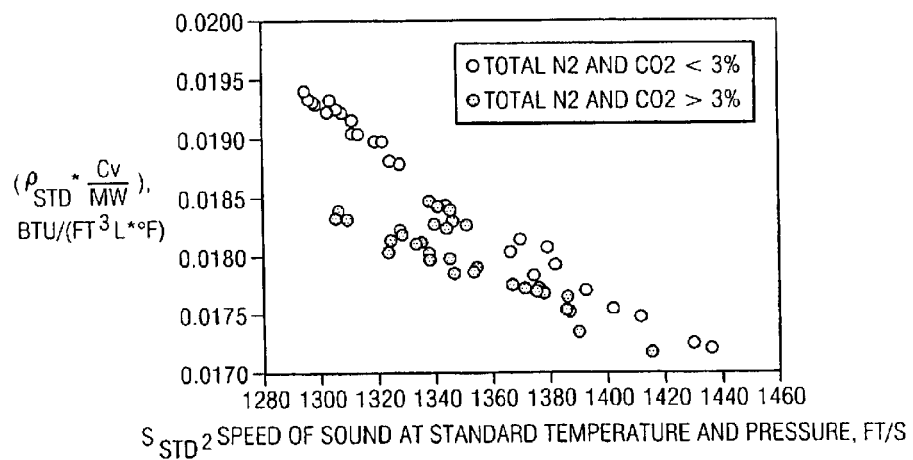
FIG. 3 illustrates the relationship between specific heat (constant volume) divided by molecular weight and speed of sound and diluent concentrations.

FIG. 3 illustrates that the product of $(\rho_{STD} * c_v/MW)$ is a function of standard sound speed and diluent concentration. As illustrated, the values for the product of standard density and the specific heat at constant volume for 86 distinct gas mixtures may be plotted against standard sound speed. The product varies with standard sound speed and the values are affected by the diluent concentration. The natural gas mixtures are composed of hydrocarbons with known concentrations of nitrogen and carbon dioxide.

Thus, the variation of the product $(\rho_{STD} * c_v/MW)$ can be modeled as a function of the standard sound speed, the diluent concentrations, and constant values. Thus:

$$(\rho_{STD}*c_v/MW)=A+B/S_{STD}+C/S_{STD}^2$$

where $$A=A_0+A_1*X_{N2}+A_2*X_{CO2}$$

$$B=B_0+B_1*X_{N2}+B_2*X_{CO2}$$

$$C=C_0+C_1*X_{N2}+C_2*X_{CO2}$$

Regression fitting may be used to calculate values for the nine constant values.

$A_0=0.00248359$
$A_1=0.000475082$
$A_2=0.000653587$
$B_0=11.0257$
$B_2=-1.67547$
$B_2=-2.3125$
$C_0=14707.8$
$C_1=1185.97$
$C_2=1598$

The model equation can now be arranged to predict the value of nitrogen concentration $X_{N2}$, given values for the standard sound speed, $S_{STD}$, and the concentration of carbon dioxide, $X_{CO2}$. Thus:

$$X_{N2}=[(Q/V*\Delta T)-(A_0+B_0/S_{std}+C_0/S_{std}^2)-X_{CO2}*(A_2+B_2/S_{std}+C_2/S_{std}^2)]/(A_1+B_1/S_{std}+C_1/S_{std}^2)$$

This equation can be used to determine nitrogen concentration from measurements of the amount of energy transferred as heat to the gas mixture, the volume of the container, the temperature rise of the gas mixture (temperature having been measured before and after heating), the standard sound speed, and the concentration of carbon dioxide.

Using the equation above, actual values of the product $(\rho_{STD}*c_v/MW)$, actual values of standard sound speed, and actual values of carbon dioxide concentration were used to calculate values of nitrogen concentration for a number of gas mixtures whose actual nitrogen concentrations were known. The calculated value of nitrogen concentration was then compared to the actual value of nitrogen concentration for each gas mixture. The agreement between the calculated and the actual values is good.

Figure 4:
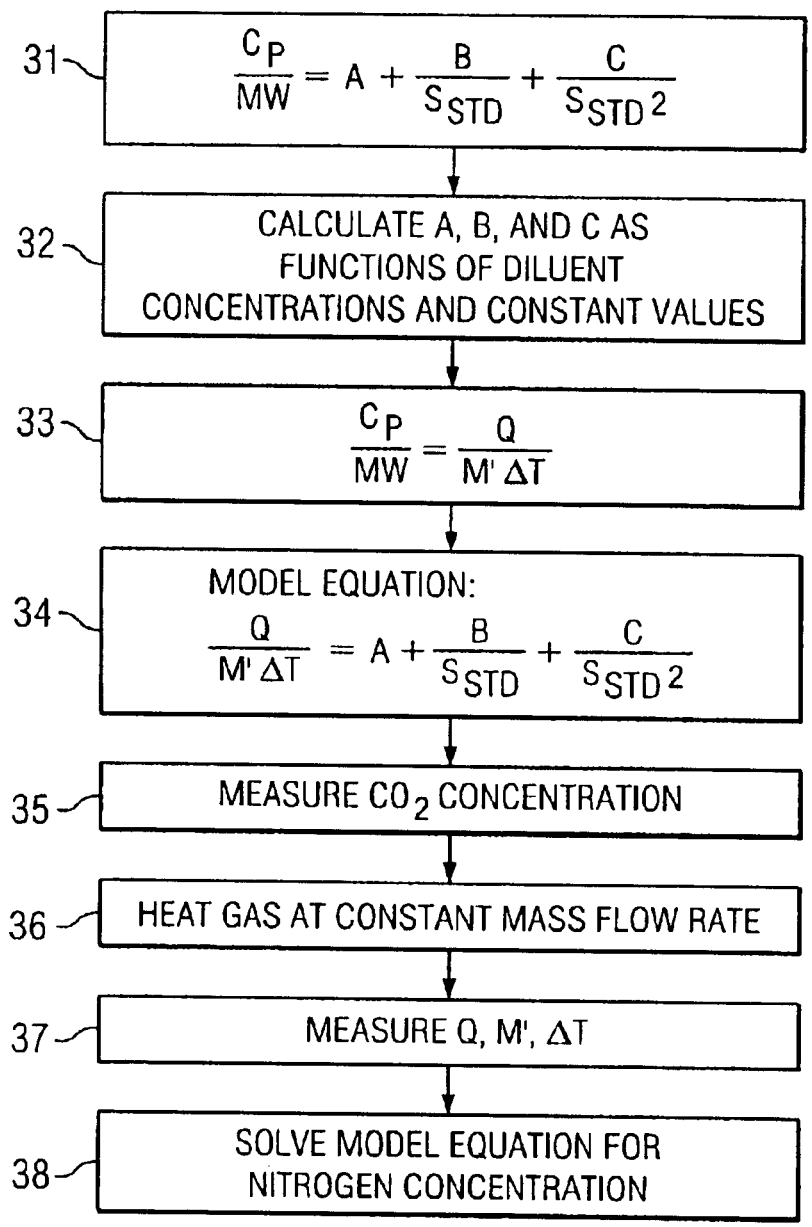
FIG. 4 illustrates a second method of determining the nitrogen concentration in a natural gas.

FIG. 4 illustrates a second embodiment of a method of determining nitrogen concentration by heating a gas mixture. This approach involves measuring the temperature rise of the gas as it flows through a chamber at a constant mass flow rate while thermal energy is added by heating. The gas flows through the chamber with a constant mass flow rate $m'=\rho*V'$ where $\rho$ is the gas density and $V'$ is the volumetric flow rate. If the heating is performed with an electrical heater, the rate of heat transfer from the electrical heating element to the gas, Q, is equal to the product of the voltage across the heater times the current through the heater. In steady state and with a steady flow of gas through the chamber, the thermal energy generated by the heating element is taken up by the gas stream and causes the temperature to rise by an amount equal to $\Delta T$. Therefore, with steady flow, and in steady state (when thermal equilibrium has been reached), the rate of heat transfer to the gas stream is $$Q=\rho*V'*(c_p/MW)*\Delta T$$

If Q and $\Delta T$ are measured and the mass flow rate, $m'=\rho*V'$ is held constant by a metering device, then the quantity $c_p/MW$ is a function of the standard sound speed, the diluent concentrations, and constant values. The same type of analytical model can be used to represent the quantity $(c_p/MW)$ as was used to represent $(\rho_{std}*c_v/MW)$ although the values of the constants calculated by regression will change. Then an equation can be written and solved for the nitrogen concentration as:

$$X_{N2}=[(Q/m'*\Delta T)-(A_0+B_0/S_{std}+C_0/S_{std}^2)-X_{CO2}*(A_2+B_2/S_{std}+C_2/S_{std}^2)]/(A_1+B_1/S_{std}+C_1/S_{std}^2)$$

As indicated above, the methods of FIGS. 1 and 2 both involve correlating heat energy of the natural gas to its standard sound speed, its diluent concentrations, and constant values. The constant values can be determined from regression analysis when properties are recognized to be a function of standard sound speed. The result is a model equation, whose values can all be known or measured to solve for the nitrogen concentration.

In both methods, some of the heat energy transferred from the heating process may be transferred to the container or heating tube and not to the gas mixture. This loss can be minimized if possible, or calibrated out of the equations so that Q represents only the heat energy transferred to the gas.

What is claimed is:

1. A method of determining the nitrogen concentration in a natural gas whose carbon dioxide concentration is known, comprising the steps of:

modeling the product of the natural gas density times its specific heat (at constant volume) divided by its molecular weight as a function of the standard speed of sound of the gas, the carbon dioxide concentration, and the nitrogen concentration, for a number of gas mixtures;

determining constant values for an equation representing the function;

heating a sample of the natural gas in a closed container having a known volume;

measuring the heat energy to raise the temperature of the natural gas a known temperature increment;

equating the product of the natural gas density times its specific heat (at constant volume) divided by its molecular weight to the heat energy divided by the product of the volume times the temperature increment, thereby obtaining a model equation; and substituting known values into the model equation to solve for the nitrogen concentration.

2. The method of claim 1, wherein the constant values are determined by statistical analysis of data from gas mixtures having known diluent concentrations.

3. The method of claim 1, wherein the primary diluents in the natural gas are carbon dioxide and nitrogen.

4. A method of determining the nitrogen concentration in a natural gas whose carbon dioxide concentration is known, comprising the steps of:

modeling the specific heat of the natural gas (at constant pressure) divided by its molecular weight as a function of the standard speed of sound of the gas, the carbon dioxide concentration, and the nitrogen concentration, for a number of gas mixtures;

determining constant values for an equation representing the function;

heating the natural gas at known constant mass flow rate;

measuring the heat energy to raise the temperature of the natural gas a known temperature increment;

equating the specific heat of the natural gas (at constant pressure) divided by its molecular weight to the heat energy divided by the product of the mass flow rate times the temperature increment, thereby obtaining a model equation; and substituting known values into the model equation to solve for the nitrogen concentration.

5. The method of claim 4, wherein the constant values are determined by statistical analysis of data from gas mixtures having known diluent concentrations.

6. The method of claim 4, wherein the primary diluents in the natural gas are carbon dioxide and nitrogen.

7. A method of determining the nitrogen concentration in a natural gas whose carbon dioxide concentration is known, comprising the steps of:

correlating specific heat of the gas (constant volume or constant pressure) divided by its molecular weight to the standard speed of sound of the gas, the carbon dioxide concentration, and the nitrogen concentration, for a number of gas mixtures;

determining a function that incorporates the correlation of the correlating step;

determining constant values for an equation representing the function;

heating a sample of the natural gas in a closed container having a known volume;

measuring the heat energy to raise the temperature of the natural gas a known temperature increment;

equating the product of the natural gas density times its specific heat (at constant volume) divided by its molecular weight to the heat energy divided by the product of the volume times the temperature increment, thereby obtaining a model equation; and substituting known values into the model equation to solve for the nitrogen concentration.

8. The method of claim 7, wherein the function represents the product of the natural gas density times its specific heat (at constant volume) divided by its molecular weight as a function of the standard speed of sound of the gas, the carbon dioxide concentration, and the nitrogen concentration, for a number of gas mixtures.

9. The method of claim 7, wherein the function represents the specific heat of the natural gas (at constant pressure) divided by its molecular weight as a function of the standard speed of sound of the gas, the carbon dioxide concentration, and the nitrogen concentration, for a number of gas mixtures.

* * * * *